United States Patent
Sabacinksi

(10) Patent No.: US 11,213,564 B2
(45) Date of Patent: *Jan. 4, 2022

(54) BUCKWHEAT HONEY AND BACITRACIN WOUND-HEALING DRESSING

(71) Applicant: SanMelix Laboratories, Inc., Hollywood, FL (US)

(72) Inventor: Kenneth A Sabacinksi, Pembroke Pines, FL (US)

(73) Assignee: SANMELIX LABORATORIES, INC., Hollywood, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/686,799

(22) Filed: Nov. 18, 2019

(65) Prior Publication Data

US 2020/0085909 A1    Mar. 19, 2020

Related U.S. Application Data

(63) Continuation-in-part of application No. 15/789,066, filed on Oct. 20, 2017, now abandoned, which is a continuation-in-part of application No. 15/010,896, filed on Jan. 29, 2016, now Pat. No. 10,500,235.

(60) Provisional application No. 62/462,027, filed on Feb. 22, 2017, provisional application No. 62/109,369, filed on Jan. 29, 2015.

(51) Int. Cl.
| | |
|---|---|
| *A61K 35/644* | (2015.01) |
| *A61K 38/12* | (2006.01) |
| *A61P 17/02* | (2006.01) |
| *A61K 9/70* | (2006.01) |
| *A61K 9/00* | (2006.01) |
| *A61K 31/121* | (2006.01) |

(52) U.S. Cl.
CPC ............ *A61K 38/12* (2013.01); *A61K 9/0014* (2013.01); *A61K 9/7007* (2013.01); *A61K 31/121* (2013.01); *A61K 35/644* (2013.01); *A61P 17/02* (2018.01)

(58) Field of Classification Search
CPC .. A61K 9/7007; A61K 9/0014; A61K 31/121; A61K 35/644; A61K 38/12; A61P 17/02
See application file for complete search history.

(56) References Cited

U.S. PATENT DOCUMENTS 4,973,466 A * 11/1990 Reich .................. A61L 26/0047
424/426
10,500,235 B2 * 12/2019 Wardell .................. A61K 33/30

OTHER PUBLICATIONS

Molan, "The evidence and the rationale for the use of honey as wound dressing", Dec. 2011, Wound Practice and Research, vol. 19 iss. 4, pp. 204-220. (Year: 2011).*
Torreya, Wound Care Product Opportunity Executive Summary, Apr. 2012, First Texas Medical Partners, LLC, pp. 1-4. (Year: 2012).*
Efem, "Clinical observations on the wound healing properties of honey", Jul. 1998, British Journal of Surgery, vol. 75, pp. 679-681. (Year: 1998).*
Ranzato et al., Honey Exposure Stimulates Wound Repair of Human Dermal Fibroblasts, Jun. 2013, Burns & Trauma, vol. 1 iss. 1, pp. 32-38.*
Fidaleo et al., Methylglyoxal: A New Weapon Against Staphylococcal Wound Infections, Feb. 27, 2010, Chem. Lett., vol. 39, pp. 322-323.*
Majtan et al., Anti-biofilm Effects of Honey Against Wound Pathogens Proteus mirabilis and Enterobacter cloacae, Mar. 11, 2013, Phytotherapy Research, vol. 28, pp. 69-75.*

* cited by examiner

*Primary Examiner* — Ali Soroush
(74) *Attorney, Agent, or Firm* — Trueba & Suarez PLLC; Darlene Barron; Roberto M. Suarez

(57) ABSTRACT

A wound healing composition and method for treating acute and chronic wounds and skin conditions includes a wound healing composition or formulation including a mixture of buckwheat honey, methylglyoxal and bacitracin.

20 Claims, 5 Drawing Sheets

A. Staphylococcus aureus

D. Streptococcus pyogenes

| No | Ingredient | Suggested Amount | Suggested Amount Range + or - 10% | Range Amount | Weight Range |
|---|---|---|---|---|---|
| 1 | Buckwheat Honey | 4 grams | 99.67 - 99.73% wt | 3.6 - 4.4 grams (+/- 10%) | 99.4 - 99.91% wt |
| 2 | Methylyoxal (MGO) | 1000 mg of MGO per kg of Honey/MGO composition | 0.09 - 0.11% wt | 500mg to 2000mg of MGO per kg of Honey/MGO composition | 0.05 - 0.2% wt |
| 3 | H₂O (Sterile) | q.s. | q.s. | q.s. | q.s. |
| 4 | Bacitracin Zinc Salt or Bacitracin 7.2mg/400mg | 500 Units (125 x 4) | 0.18 - 0.22% wt per gram of honey | 10 units to 250 units | 0.02 - 0.4% wt per gram of honey |
| 5 | Hydrochloric Acid | q.s. | q.s. | q.s. | q.s. |

Fig. 5

BUCKWHEAT HONEY AND BACITRACIN WOUND-HEALING DRESSING

CROSS-REFERENCE TO RELATED APPLICATIONS

This application is a Continuation-in-Part of, and claims priority to, U.S. patent application Ser. No. 15/789,066, filed on Oct. 20, 2017, which claims the benefit under 35 U.S.C. § 119(e) to U.S. Provisional Patent Application No. 62/462,027, filed on Feb. 22, 2017. U.S. patent application Ser. No. 15/789,066 is a Continuation-In-Part of, and claims priority to, U.S. patent application Ser. No. 15/010,896, filed on Jan. 29, 2016, which claims the benefit under 35 U.S.C. § 119(e) to U.S. Provisional Patent Application No. 62/109,369, filed Jan. 29, 2015. These applications are incorporated by reference as if fully set forth herein.

FIELD OF THE INVENTION

The present invention generally relates to wound healing compositions, more specifically to wound healing compositions including various combinations of medicinal honey combined with bacitracin and methylglyoxal, pharmaceutically acceptable carriers, inorganic minerals with methylglyoxal salts, and medicinal buckwheat honey.

BACKGROUND OF THE INVENTION

Honey has been used as a medicinal aid since ancient times and has been well established in its ability to successfully treat acute and chronic wounds. Honey has been found to be effective in reducing infection and aiding healing. Honey obtained predominately from one flower source is considered monofloraL Individual honeys obtained from a single flowering plant species (monofloral honeys) have specific characteristics, which allows a monofloral honey to be utilized as a therapeutic substance. Monofloral honeys also have a high level of antioxidants, which helps prevent the cell damage caused by reactive oxygen species and have been well documented to have excellent broad spectrum antibacterial and antifungal properties. As a result of these findings, numerous studies have been conducted to understand the efficacy of monofloral buckwheat honey in treating acute and chronic wounds.

Buckwheat honey has been well known in the holistic medicine world as a medicinal aid because it has a high mineral content, antioxidant compounds, and healing properties. Physically, buckwheat honey is characterized as having a dark brown color with a red tint and is also known for a unique, woody aroma. Chemically, buckwheat honey is a complex mixture of fructose, glucose, sucrose, and water, and it particularly has higher concentrations of macronutrients, various trace elements, and antioxidant compounds. To create this complex mixture, honeybees collect nectar, and through digestion the honeybees add unique digestive proteins, which gives the honey its unique healing characteristics.

Various honeys have been shown to be safe and an effective dressing for skin ulcerations, including Wagner grade-II diabetic foot ulcers. Additionally, dressings using honey have shown decreased wound edema and reduced odor more effectively than non-honey dressings. Buckwheat honey provides characteristics that provide effective and broad spectrum antibacterial activity and antifungal properties. See, FIGS. 1 to 4, where the antibacterial effectiveness of each of willow herb honey, heather honey, buckwheat honey, lingonberry honey, and cloudberry honey against *Staphylococcus aureus*, MRSA, *Streptococcus pneumoniae*, and *Streptococcus pyogenes*, respectively, is shown. Huttunen S, Riihinen K, Kauhanen J, Tikkanen-Kaukanen, C. Antimicrobial activity of different mono floral honeys against human pathogenic bacteria. APMIS: acta pathologica, microbiologica, et immunological Scondinavica. Sep., 2013, 121(9): 827-834. In addition, buckwheat honey has a higher concentration of polyphenols and $H_2O_2$ (hydrogen peroxide) and has other healing properties.

Brudzynski, K, et aL, Powerful bacterial killing by buckwheat honeys is concentration-dependent, involves complete DNA degradation and requires hydrogen peroxide. Frontiers in Microbiology July 2012; Vol 3, Article 242, reported the effectiveness of buckwheat honey's antibacterial effect through its high concentration of hydrogen peroxide. The study reported that buckwheat honey uses the bactericidal effects of hydroxyl radicals while maintaining an antioxidant concentration sufficiently high to prevent cellular damage. By implementing this very unique mechanism, buckwheat honey is able to kill bacteria while protecting bodily tissues from the oxidative stress used to kill the microorganisms.

In terms of application, a study reported in Van den Berg et aL, An in vitro examination of the antioxidant and anti-inflammatory properties of buckwheat honey. Journal of Wound Care, VoL 17, No. 4, April 2008, pp. 172-178, looked at the effectiveness of different types of honey on wound healing. The study considered the different ways that honey could promote healing in injured tissue. After compiling all of the data, the authors found that buckwheat honey was the most effective wound-healing honey.

In an article discussing the mechanism of how honey induces wound repair, it was shown that buckwheat honey has an ability to promote cellular regeneration superior to other healing remedies, specifically manuka honey. Ranzato E, Martinotti S, Burlando B. Epithelial mesenchymal transition traits in honey-driven keratinocyte wound healing: Comparison among different honeys. Wound Repair Regen. 2012; 20:778-85. doi: 10.1111/j.1524-475X.2012.00825.x. [PubMed].

In a Finnish study, five different honeys were used in concentrations of 60%, 40%, and 20% by weight in phosphate buffered saline. The highest antimicrobial activity was recorded when the honey had a concentration of 40% or 60% by weight, but significant antimicrobial activity was also detected even when the honey was at 20% concentration by weight. Sanna Uttunen, et aL, "Antimicrobial activity of different Finnish monofloral honeys against human pathogenic bacteria." ACTA Pathologica Microbiologica Et Immunologica Scandinavica, 2012, pages 827-834.

Honey has been used in clinical practice for many types of diseases since ancient times. It is still being used because it enhances auto-debridement by absorbing edematous fluid due to its high osmolarity. Van den Berg et al. data demonstrated that honey exposure induces low cytotoxicity on fibroblasts. This finding confirms previous results on keratinocytes' increased ability to regenerate epithelial cells, suggesting that honey can be considered a safe compound for external applications. Scratch wound data and cell migration assay showed that honey improves fibroblast wound repair capabilities. Cell motility is a key element of tissue repair processes. Therefore, its increased induction could explain the ability of honey to promote the activation of fibroblasts at a faster rate, similar to what was reported for keratinocytes.

To understand the mechanisms underlying this effect, i.e., promoting the activation of fibroblasts at a faster rate, various studies used a battery of inhibitors of cell signaling pathways that are known to be directly involved in the wound healing process. BAPTA-AM (1,2-bis(2-aminophenoxy)ethane-N,N,N',N'-tetraacetic acid tetrakis(acetoxymethyl ester)) was found to be the most effective inhibitor of scratch wound closure, showing the essential role of intracellular calcium in the wound-healing process. Current literature provides evidence that matrix metalloproteinases (MMPs) and their inhibitors are essential in tissue repair. MMPs and tissue inhibitors of metalloproteinases (TIMPs) are known to control the inflammatory phase of wound healing by modulating chemokine and cytokine activation. They also regulate matrix degradation and remodeling, which is an essential step in wound repair. Majtan and Ranzato have consistently demonstrated that honey exposure induces gelatinase MMP-9 expression in human keratinocytes, which confirms a similar mechanism already observed on platelet lysate added cells. In contrast, the platelet lysate does not seem to affect gelatinase expression in fibroblasts. Ranzato E, Martinotti S, Volante A, Mazzucco L, Burlando B. Platelet lysate modulates MMP-2 and MMP-9 expression, matrix deposition and cell-to-matrix adhesion in keratinocytes and fibroblasts. Exp Dermatol 2011; 20:308-13. doi: 10.1111/j.1600-0625.2010.01173.x. [PubMed]. This is another point of convergence with the present investigation, where MMP or TIMP upregulation by honey was limited to MMP-3 induction with manuka, and TIMP-1 with manuka and buckwheat. The increase of TIMP-1 upon buckwheat exposure could be linked to the anti-inflammatory effects of this protein, considering that it has been induced by cytokine exposure in dermal fibroblasts.

Studies consistently indicate that honey is generally active in facilitating wound closure or healing, thus confirming much anecdotal and scientific evidence. However, a key finding is that different types of honey work through different mechanisms, and some of these mechanisms are more efficient and effective than others. In particular, buckwheat honey has shown more powerful wound-healing properties than manuka honey on both dermal and epidermal cells. Hence, the complex of different honey types offers a wider set of therapeutic possibilities, raising new medical interest in this valuable natural product. See, Elia Ranzato, et al., "Honey exposure stimulates wound repair of human dermal fibroblasts." Burns & Trauma, June 2013, Vol 1, Issue 1. It is nature's invention of a natural wound healing dressing. When buckwheat honey is combined with bacitracin, results are significantly improved.

Bacitracin is a mixture of related antimicrobial cyclic peptide factions produced by organisms of the licheniformis group of Bacillus subtilis var Tracy, first isolated in 1945. These peptides disrupt both gram positive and gram negative bacteria by interfering with cell wall and peptidoglycan synthesis.

Bacitracin is primarily used as a topical preparation in ointment form.

The combination of buckwheat honey and bacitracin offers overlapping benefits in wound treatment.

Bacitracin, often in combination with other topical antibiotics, is typically used as an ointment for topical treatment of a variety of localized skin or eye infections as well as for the prevention of wound infections. A non-ointment form of ophthalmic solution is available to treat eye infections.

Bacitracin can be loaded into hydrogels, carboxyethyl cellulose (CMC), polyvinyl alcohol (PVA), gelatin, and crosslinked polyacrylamide. When bacitracin is used with CMC/PVA, there is a higher rate of release. When bacitracin is used with a greater amount of gelatin, there is a slower release, which is effective for diaper rash, dermatitis, Tinea, and athlete's foot infection. Bacitracin may also be used for minor wounds as a dressing and may be applied to the skin as a liquid, gel, cream, or ointment.

OBJECTS OF THE INVENTION

It is an object of the invention to provide a wound-healing or skin condition treatment formulation or composition consisting essentially of buckwheat honey and one or more bacterial agents, such as bacitracin.

It is a yet further object of the invention to provide a wound-healing or skin condition treatment formulation or composition consisting essentially of about 5 units to about 500 units of bacitracin per gram of honey, preferably from about 7.5 units to about 150 units of bacitracin per gram of honey.

It is a yet further object of the invention to provide a wound-healing or skin condition treatment formulation or composition wherein the bacitracin is in the form of white powder or in liquid, gel, cream, or ointment form.

It is a yet further object of the invention to provide a wound-healing or skin condition treatment formulation or composition which can be provided in a tube or spray.

It is a yet further object of the invention to provide a wound-healing or skin condition treatment dressing comprising substrate material and an effective amount of a wound-healing or skin condition treatment formulation comprised of buckwheat honey and one or more bacterial agents.

It is a yet further object of the invention to provide a wound-healing or skin condition treatment dressing wherein wound-healing or skin condition treatment formulation or composition is impregnated into a reinforcing fiber substrate or bandage for application to a wound or a patient's skin and can be released from the reinforcing fiber substrate.

It is a yet further object of the invention to provide a method of treating a wound or skin condition on or in a patient which comprises directly applying to the wound or the patient's skin an effective amount of a wound-healing or skin condition treatment formulation or composition comprised of buckwheat honey and bacitracin.

It is a yet further object of the invention to provide a method of treating a wound or skin condition on a patient which comprises contacting the wound or the patient's skin with a wound-healing or skin condition treatment dressing comprising substrate material and an effective amount of wound-healing or skin condition treatment formulation or composition comprised of buckwheat honey and bacitracin.

These and other objects of the invention will become more apparent from the discussion below.

SUMMARY OF THE INVENTION

The novel and unique combination of buckwheat honey, methylglyoxal, and an antibacterial agent such as bacitracin offers overlapping benefits in wound treatment or in treating skin conditions. The invention herein relates to the specific use of a composition or formulation comprising buckwheat honey and methylglyoxal with one or more antibacterial compounds such as bacitracin for use directly on wounds or on a patient's skin, or on or in a dressing applied to a wound or a patient's skin. The composition can be impregnated on a bandage or dressing substrate such as acetate, cotton, or other material useful to carry the composition. When used directly on a wound or a patient's skin, the formulation or composition preferably includes a gelling agent that thickens the composition.

The combination of buckwheat honey, methylglyoxal ("MGO"), and bacitracin as an antibacterial formulation or composition is a preferred embodiment that provides a potent wound care therapy or skin condition treatment with unique healing qualities. It offers broad spectrum antibacterial activity along with antifungal and antiviral properties. This combination gives antibacterial effects that are effective on, for example, methicillin resistant *Staphylococcus aureus*. Each gram of the buckwheat honey and MGO ("honey-MGO") combined with bacitracin, yielding a honey-MGO-bacitracin formulation, will have a bacitracin concentration in the range of from about 5 units to about 500 units, preferably from about 7.5 units to about 150 units. This range will augment the antibacterial properties of the buckwheat honey. A unit, or International Unit, comprises about 0.0182 mg of the International Standard for bacitracin.

Potential uses include, but are not limited to, skin irritation, rashes, dermatitis, pruritus, fungal infection, diaper rash, minor skin infections, burns (minor and severe), ulcerations (superficial, deep, and to all depth levels), surgical wounds, traumatic wounds, gunshot wounds, puncture wounds, chemical burns, insect bites, animal bites, draining, and non-draining wounds, neuropathic and vascular wounds, decubitus wounds, and other skin conditions and acute and chronic wounds.

In an aspect of the invention, a therapeutic wound-healing or skin condition treatment formulation or composition comprises a wound-healing or skin condition treating effective amount of buckwheat honey and one or more antibacterial agents.

In another aspect of the invention, a therapeutic wound-healing or skin condition treatment formulation or composition comprises a wound-healing or skin condition treating effective amount of buckwheat honey and bacitracin.

In a further aspect of the invention, in a wound-healing or skin condition treatment formulation or composition, the buckwheat honey is 100% pure and strained.

In a further aspect of the invention, a wound-healing or skin condition treatment formulation or composition is applied directly to a wound or the patient's skin.

In a further aspect of the invention, in a wound-healing or skin condition treatment formulation or composition, bacitracin is present in an amount of from about 5 units to about 500 units per gram of buckwheat honey.

In a further aspect of the invention, in a wound-healing or skin condition treatment formulation or composition, bacitracin is present in an amount of from about 7.5 units to about 150 units per gram of buckwheat honey.

In a further aspect of the invention, a dose of a wound-healing or skin condition treatment formulation or composition comprises about four grams of buckwheat honey.

In a further aspect of the invention, a wound-healing or skin condition treatment formulation or composition includes a gelling agent.

It is a yet further aspect of the invention to provide a wound-healing or skin condition treatment formulation or composition wherein the gelling agent is sufficient to thicken the mixture and to substantially prevent the formulation or composition from running and to release a desired amount of the formulation or composition to the wound or skin condition.

In a further aspect of the invention, a wound-healing or skin condition treatment formulation or composition can be provided in a tube or spray.

In a further aspect of the invention, a wound-healing or skin condition treatment dressing comprises a bandage or substrate material and an effective amount of a wound-healing or skin condition treatment formulation or composition comprised of buckwheat honey and one or more bacterial agents.

In a further aspect of the invention, a wound-healing or skin condition treatment dressing comprises a bandage or reinforcing fiber substrate material and a wound-healing or skin condition treatment formulation or composition comprised of buckwheat honey and bacitracin.

In a further aspect of the invention, a wound-healing or skin condition treatment bandage or dressing comprises an effective amount of the wound-healing or skin condition treatment formulation or composition.

In a further aspect of the invention, in a wound-healing or skin condition treatment dressing, the substrate material comprises acetate, cotton (medical gauze), or alginate.

In a further aspect of the invention, a wound-healing or skin condition treatment dressing comprises a 5'×4" adhesive or non-adhesive bandage with from about 2 to about 8 grams of wound-healing or skin condition treatment formulation or composition.

In a further aspect of the invention, a wound-healing or skin condition treatment bandage or dressing comprises about four grams of wound-healing or skin condition treatment formulation or composition.

In a further aspect of the invention, in a wound-healing or skin condition treatment bandage or dressing, the wound-healing or skin condition treatment formulation or composition is impregnated into a bandage or reinforcing fiber substrate for application to a wound or a patient's skin and is released from the bandage or reinforcing fiber substrate.

In a further aspect of the invention, a method of treating a wound on or in a patient or a skin condition on a patient's skin comprises directly applying an effective amount of a wound-healing or skin condition treatment formulation or composition comprised of buckwheat honey and bacitracin.

In a further aspect of the invention, a method of treating a wound or skin condition on a patient comprises contacting the wound or skin condition with a wound-healing or skin condition treatment bandage or dressing comprising a reinforcing fiber substrate material and a wound-healing or skin condition treatment formulation or composition comprised of buckwheat honey and bacitracin.

In a further aspect of the invention, the buckwheat honey and bacitracin formulation or composition is applied in a cream.

In a further aspect of the invention, the buckwheat honey and bacitracin formulation or composition is applied in an ointment.

These and other advantages of the present invention will be readily appreciable from the following description of preferred embodiments of the invention and from the accompanying drawings and claims.

BRIEF DESCRIPTION OF THE DRAWINGS

In the accompanying figures, like reference numerals refer to identical or functionally similar elements throughout the separate views. The accompanying figures, together with the detailed description below are incorporated in and form part of the specification and serve to further illustrate various embodiments and to explain various principles and advantages all in accordance with the present invention, in which:

FIG. 5 is a table showing the composition of a buckwheat honey-methylglyoxal-bacitracin wound healing composition, according to an embodiment of the invention.

Figure 1:
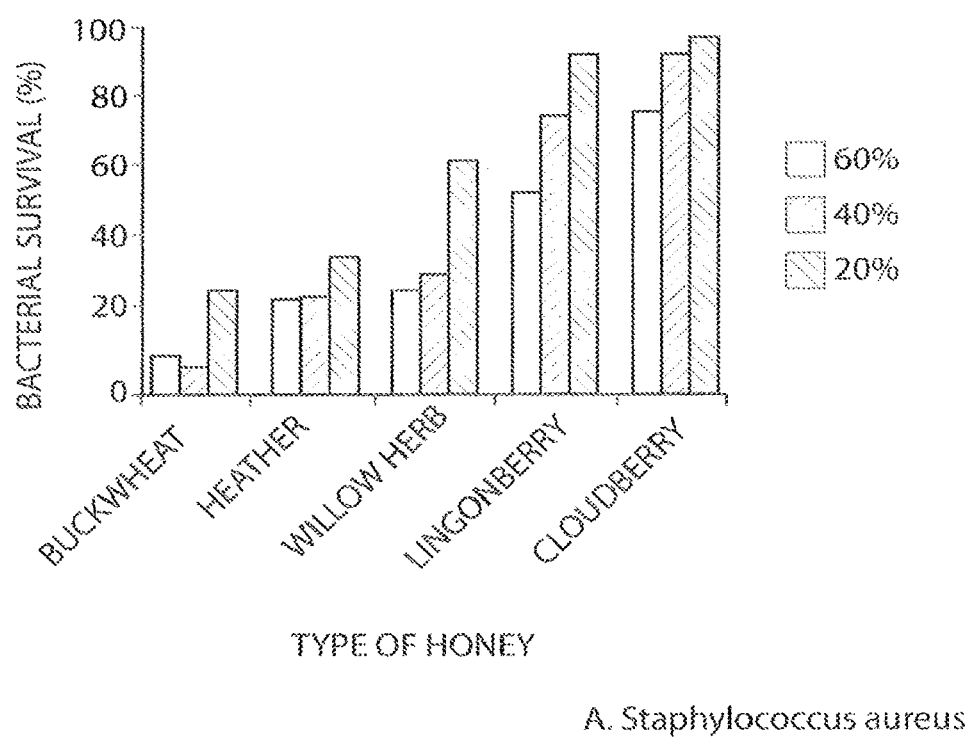
FIG. 1 is a graph representing the antibacterial effectiveness of buckwheat honey, heather honey, willow herb honey, lingonberry honey, and cloudberry honey, respectively, against *Staphylcoccus aureus*.
Figure 2:
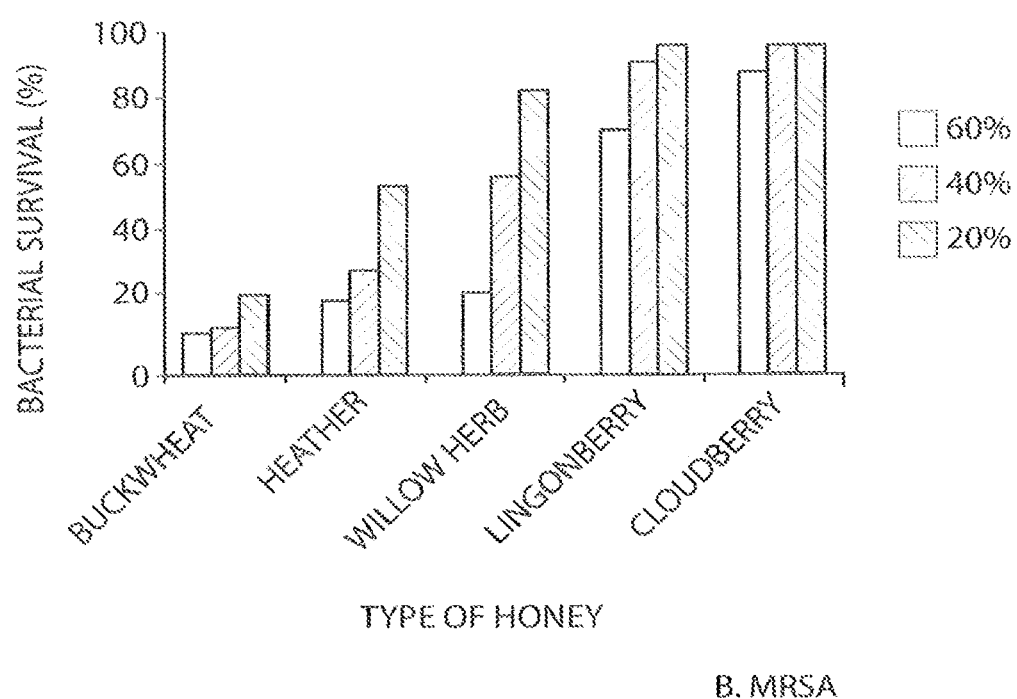
FIG. 2 is a graph representing the antibacterial effectiveness of buckwheat honey, heather honey, willow herb honey, lingonberry honey, and cloudberry honey, respectively, against MRSA.
Figure 3:
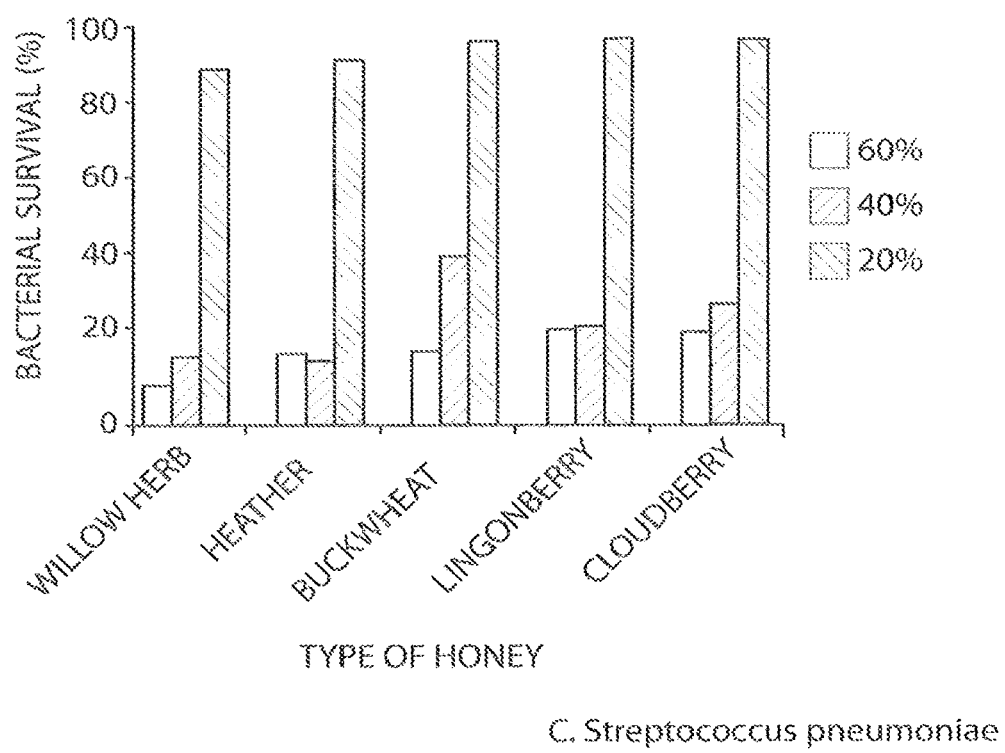
FIG. 3 is a graph representing the antibacterial effectiveness of buckwheat honey, heather honey, willow herb honey, lingonberry honey, and cloudberry honey, respectively, against *Streptococcus pneumoniae*.
Figure 4:
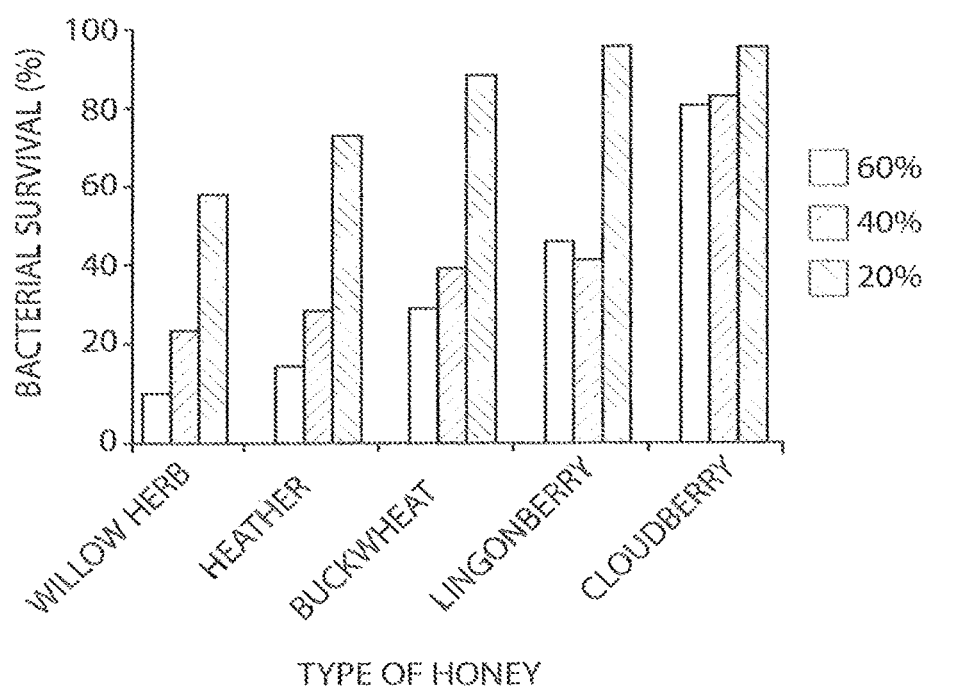
FIG. 4 is a graph representing the antibacterial effectiveness of buckwheat honey, heather honey, willow herb honey, lingonberry honey, and cloudberry honey, respectively, against *Streptococcus pyogenes*.

While the invention as claimed can be modified into alternative forms, specific embodiments thereof are shown by way of example in the drawings and will herein be described in detail It should be understood, however, that the drawings and detailed description thereto are not intended to limit the invention to the particular form disclosed, but on the contrary, the intention is to cover all modifications, equivalents and alternatives falling within the scope of the present invention.

DETAILED DESCRIPTION

Unless defined otherwise, all technical and scientific terms used herein have the same meaning as commonly understood to one of ordinary skill in the art to which this invention belongs. Although any methods, devices or materials similar or equivalent to those described herein can be used in the practice or testing of the invention, the preferred methods, devices, and materials are now described.

The term "wound-healing or skin condition treatment formulation or composition" as used herein refers to a formulation or composition designed to treat wounds, lesions, skin conditions, or injuries caused by physical, metabolic, or chemical means. The wound-healing or skin condition treatment process comprises a series of steps where injured tissue is repaired or regenerated. This usually involves three steps: (a) an inflammation stage (0-3 days), (b) a cellular proliferation phase (3-12 days), and (c) a remodeling phase (3-6 months).

Typically a wound-healing or skin condition treatment formulation or composition has at least one active ingredient that helps to repair a wound or treat a skin condition. Examples of active ingredients include, but are not limited to, bacitracin, methylglyoxal, bacitracin, neomycin, and polymyxin (e.g., polymyxin B sulfate). A wound-healing or skin condition treatment formulation or composition may also contain inactive ingredients that are typically required for formulation. (See, e.g., U.S. Pat. No. 5,652,274 and U.S. Published Patent Application No. 2005/0043253, each of which is incorporated herein by reference.)

Healing time related to wounds or skin conditions, whether acute or chronic, depends on multiple factors. These factors include, but are not limited to, patient medical history, etiology, location, size, depth, length of time present, previous treatment, and drainage (purulent, synovial, serous, and serosanguinous).

As discussed above, wound-healing or skin condition treatment normally progresses through different phases. Wounds and skin conditions will heal in days to months. Healing may be delayed for any number of reasons. Some of these reasons include, but are not limited to, poor circulation, infection, elevated protease levels, pressure (weight-bearing), increased motion, patient non-compliance, and the like.

A "chronic wound," "non-healing wound," slow-to-heal wound," or "stalled wound," as used herein, refers to a wound that fails to heal over a 4 to 12 week timeframe from inception of the wound to complete closure of the skin at the wound site. Such wounds commonly include external dermal wounds.

Skin wounds designated as "chronic", "non-healing", "slow-to-heal", or "stalled" are commonly observed in clinical settings as venous leg ulcers, diabetic foot ulcers, pressure ulcers, arterial ulcers, ulcers of mixed etiology, burns, or non-healing surgical wounds. Other types of non-healing wounds or conditions are observed in less frequent conditions, such as, fistulae, dermatitis or vasculitis wounds, skin cancers, and radiation burns. This list is not exhaustive and is provided to show examples of such non-healing wounds or skin conditions. These wounds or skin conditions are differentiated from "acute" wounds or skin conditions that spontaneously heal without complications in a matter of days or weeks through the four normal phases of the "wound-healing curve" (hemostasis, inflammation, proliferation, and remodeling). Chronic wounds or skin conditions may persist for months or years and occasionally can last a lifetime and are therefore commonly referred to as "non-healing" wounds. There is a need for treatment of any of these types of non-healing wounds or skin conditions since spontaneous healing has failed to occur. In chronic wounds or skin conditions, at the cellular biological level, there is commonly a prolonged inflammatory phase often caused by elevated proteases or active infection.

Since it was developed, bacitracin has been used for the treatment of all types of wounds. Wounds such as vascular (arterial and venous), neuropathic, pressure, traumatic, post-operative, and infected wounds responded to treatment with bacitracin. In addition, treatment with bacitracin included wounds of varying depths ranging from pre-ulceration, superficial, and deep to ulcerations that extend to the tendons, joints, and bones.

During clinical treatment of all types and depths of wounds, treatment protocol was developed using a dilution of bacitracin. Various dilutions of bacitracin have been clinically tested. A typical useful dilution is 50,000 units of bacitracin in 9.8 ml of sterile water, which seemed to have the best reproducible effects on wound healing. There is no decrease in the antimicrobial properties of bacitracin at this dilution. In addition, there has been no bacterial resistance found or developed to bacitracin.

Further research and clinical case studies conducted on preventing and treating wounds, preventing chronicity of wounds, promoting antioxidation of healthy cells and tissue, and facilitating faster healing led to investigation of the combination of honey with bacitracin. Earlier studies used generic honey (sugar) and bacitracin in no specific combination or dilution. Buckwheat honey (*fagopyrum esculentum*) showed increased antioxidant, anti-inflammatory, and at least equal antibacterial properties as compared to other mono-floral honeys. The unique combination of buckwheat honey and bacitracin creates specific and unique benefits to wound healing. The buckwheat honey/bacitracin formulation or composition is for use in direct application or as part of a wound dressing for treatment of all types and depths of wounds and acute or chronic skin conditions or skin ulcerations regardless of vascular and neurologic status.

An embodiment of a buckwheat honey/bacitracin formulation or composition according to the invention comprises a medicinal honey with concentrations of hydrogen peroxide and polyphenols that are all in the upper concentration range of what are naturally found in various native honeys. In this first formulation, buckwheat honey provides a composition containing buckwheat honey with high natural concentrations of hydrogen peroxide and polyphenols to which bacitracin is added in a concentration of from about 5 to about 500 units per gram of honey. The phrase "high natural concentrations of hydrogen peroxide and polyphenols" is defined as concentrations that naturally exist in buckwheat honey where the concentration of hydrogen peroxide is in the range of about 2-4 mM and where the polyphenol concentration is in the range of about 275-575 gallic acid equivalents per gram of honey.

The buckwheat honey useful according to the invention is pure and strained, preferably seasonally harvested raw, monofloral buckwheat honey naturally rich in hydrogen peroxide (containing and/or capable of generating about 2-4 mM concentration of hydrogen peroxide), polyphenols (275-575 gallic acid equivalents of polyphenol compounds per gram of honey). Buckwheat honey, which is derived from the buckwheat flower, is dark brown with a red tint and typically has a pH of from about 3.0 to about 7.5. It has a shelf-life of two or more years if stored in a sealed container at from about 0.degree. to 10.degree. C. Useful buckwheat honey comprises medicinal grade, pure, unheated, microfiltered buckwheat honey such as is commercially available from, for example, Hackenberg Apiaries, Lewisburg, Pa., and other commercial apiaries.

In another aspect of the invention, a wound-healing or skin condition treatment composition or formulation is applied directly to a wound or skin condition.

In another aspect of the invention, in a wound-healing or skin condition treatment composition or formulation, bacitracin is present in an amount of from about 5 units to about 500 units per gram of buckwheat honey.

In another aspect of the invention, in a wound-healing or skin condition treatment composition or formulation, bacitracin is present in an amount of from about 7.5 units to about 150 units per gram of buckwheat honey.

In another aspect of the invention, in a wound-healing or skin condition treatment composition or formulation, 50,000 units of bacitracin in 9.8 ml of sterile water are mixed with three liters of buckwheat honey.

In another aspect of the invention, a wound-healing or skin condition treatment composition or formulation includes a gelling agent.

In another aspect of the invention, a wound-healing or skin condition treatment composition or formulation can be provided in a tube or spray.

In another aspect of the invention, in a wound-healing or skin condition treatment composition or formulation, the gelling agent is sufficient to thicken the mixture and to substantially prevent the composition from running and to release a desired amount of the dressing to the wound or skin condition.

In another aspect of the invention, a wound-healing or skin condition treatment bandage or dressing comprises a reinforcing fiber substrate material and a wound-healing or skin condition treatment composition or formulation comprised of buckwheat honey and bacitracin.

In another aspect of the invention, a wound-healing or skin condition treatment bandage or dressing comprises an effective amount of the wound-healing or skin condition treatment composition or formulation.

In another aspect of the invention, in a wound-healing or skin condition treatment dressing, the substrate material comprises acetate, cotton (medical gauze), or alginate.

In another aspect of the invention, a wound-healing or skin condition treatment bandage or dressing comprises a 2×2 adhesive bandage with from about 2 to about 6 grams of wound treatment dressing.

In another aspect of the invention, a wound-healing or skin condition treatment bandage or dressing comprises about four grams of wound treatment dressing.

In another aspect of the invention, in a wound-healing or skin condition treatment dressing, the wound-healing or skin condition treatment composition or formulation is impregnated into a bandage or reinforcing fiber substrate for application to a wound or skin condition and is released therefrom.

In another aspect of the invention, a method of treating a wound on or in a patient or a skin condition on a patient comprises directly applying an effective amount of a wound-healing or skin condition treatment composition or formulation comprised of buckwheat honey and bacitracin.

In another aspect of the invention, a method of treating a wound on a patient comprises contacting the wound with a wound treatment substrate comprising a bandage or reinforcing fiber substrate material and a wound treatment composition or formulation comprised of buckwheat honey and bacitracin.

In another embodiment of the invention, a wound healing composition consists essentially of: a buckwheat honey and methyglyoxal composition ("honey-MGO") wherein the methylglyoxal is in an amount of from about 500 to about 2000 mg per kg of the total honey-MGO composition and a dilution of bacitracin in sterile water, in an amount effective to promote wound healing. The bacitracin can be in powder form prior to dilution with sterile water. An exemplary amount for dilution is 5000 units of bacitracin per ml of sterile water.

In another embodiment of the invention, a wound healing dressing includes the honey-MGO-bacitracin wound healing composition and a support applied to a wound until healed. The support can be a fibrous gauze material, a hydrogel, a foam, a film, a hydrocolloid, a collagen, an alginate, and a combination of two or more thereof. The support can be impregnated with a pharmaceutically-acceptable amount of the honey-MGO-bacitracin wound healing composition.

A method for treating a wound includes the steps or acts of: providing a honey-MGO-bacitracin would healing composition and contacting the wound with a pharmaceutically-acceptable amount of the composition to promote healing of the wound.

In another embodiment, the method for treating a wound can include providing a carrier dressing support impregnated with a pharmaceutically-acceptable amount of the honey-MGO-bacitracin wound healing composition and applying the carrier dressing support to a wound such that the wound healing composition is substantially in contact with the wound. The carrier dressing can be changed daily, every two days, every three days, or as needed until the wound is healed.

Bacitracin is a natural antibacterial compound. It typically is a white powder with a pH of from about 1.5 to about 5.0, ideally about 4.5, when diluted in sterile water. Bacitracin has a shelf-life of about 12 months if stored in a light-resistant container at a temperature not to exceed about 35. degree. C. Bacitracin is commercially available, for example, as EVOPURE® from TOKU-E.

A useful preparation comprising buckwheat honey and bacitracin comprises bacitracin in a concentration of from about 5 units to about 500 units, preferably about 7.5 units to about 150 units, per gram of honey in the final honey product. This buckwheat honey/bacitracin composition has broad-spectrum antimicrobial activity effective to reduce the number of viable microorganisms at a wound site.

The buckwheat honey/bacitracin formulations or compositions are used in aqueous, ointment, or wound-dressing compositions or formulations to modulate biochemical mechanisms associated with wound healing, including decreasing both wound protease activities and active infection.

The buckwheat honey/bacitracin formulations or compositions can be applied directly to a wound or skin condition. In another aspect, the present invention provides a bandage or dressing for wound healing or treatment of a skin condition. The bandage or dressing comprises one or more of the buckwheat honey/bacitracin formulations or compositions described herein and a support or substrate. In any embodiment of the dressing, the support or substrate includes, but is not limited to, a fibrous gauze material, a hydrogel, a foam, a film, a hydrocolloid, an alginate, a collagen, or a combination of any two or more of the aforementioned. Useful bandages or dressings include BAND-AID® or similar bandages that comprise adhesive backings with cotton or other material that adheres to the adhesive backings and absorbs the buckwheat honey/bacitracin formulations or compositions.

In another aspect of the invention, a wound or skin condition is treated with a buckwheat honey/bacitracin formulation or composition described herein.

In another embodiment of the buckwheat honey/bacitracin formulation or composition, the various compositions are used prophylactically to prevent surgical wounds in high-risk patients from post-operative wound dehiscence and non-healing. More than 53 million people undergo surgical procedures annually in the United States, with about half of these occurring under general anesthesia. Post-operative wound dehiscence has been investigated in several studies, and a small incidence has shown to be an issue of concern in all age groups, including the pediatric population, but with a higher incidence in the older population. The failure of these surgical wounds to heal in a normal time frame pushes them into the category of chronic wounds. Diabetes, obesity, cancer therapy, and vascular abnormalities, which are all increasing in incidence in the Western population, contribute to delayed healing and are considered risk factors. The prophylactic application of one or more of the buckwheat honey/bacitracin formulations herein to surgical incisions post-operatively in "high-risk" patients will aid in reducing the incidence of non-healing surgical wounds.

The components of the buckwheat honey/bacitracin formulation or composition surprisingly provide a synergistic effect that results in the suppression of the accumulation of a biochemical marker (e.g., proteases, and pro-inflammatory cytokines) associated with inflammation, and the up-regulation of other biochemical markers (e.g. growth factors and protease inhibitors) associated with wound healing. In addition, the components of the buckwheat honey/bacitracin formulations or compositions provide antibacterial activity that acts concomitantly with the anti-inflammatory activity to also provide suppression of active infections.

In some aspects of the invention pH adjusters may be needed and used in an amount which produces the desired function provided the amount of the pH adjuster does not affect the stability of composition. These pH adjusters are acids or bases that can be used to adjust the pH of the finished composition or formulation to a desired leveL Examples of useful pH adjusters include, but are not limited to, acetic acid, ammonia, citric acid, ethanolamine, formic acid, oxalic acid, potassium hydroxide, sodium hydroxide, and triethanolamine. The pH adjusters are used in an effective, pH-adjusting amount of, for example, from about 0.01 to about 2.0% by weight, preferably from about 0.05 to about 1.0% by weight, based upon the desired effect. If buffering agents are required, the compounds can be used to maintain a desired pH in an aqueous environment. Examples of such buffers include, but are not limited to, boric acid, citric acid, lactic acid, fumaric acid, phosphoric acid, and salts thereof. The buffering agents are used in an effective, buffering amount of, for example, from about 0.01 to about 2.0% by weight, preferably from about 0.05 to about 1.0% by weight, based upon the desired effect.

In another aspect of the invention, the buckwheat honey/bacitracin formulation or composition may additionally compromise one or more hemostatic agents. Examples of such hemostatic agents include, for example, extracellular matrix protein, kaolin, zeolite, chitosan, anhydrous aluminum sulfate, and aluminum chloride hexahydrate. The hemostatic agents are used in an effective, hemostatic amount of, for example, from about 0.01 to about 2.0% by weight, preferably from about 0.05 to about 1.0% by weight, based upon the desired effect.

In another aspect of the invention addition, the buckwheat honey/bacitracin formulation or composition may additionally compromise one or more anesthetic agents. Examples of such anesthetic agents include, but are not limited to, lidocaine 1% and 2%, with and without epinephrine, and bupivacaine 0.25% and 0.5%, with and without epinephrine. The anesthetic agents are used in an effective, anesthetic amount, for example, from about 0.01 to about 2.0% by weight, preferably from about 0.05 to about 1.0% by weight, based upon the desired effect.

In another aspect of the invention, the buckwheat honey/bacitracin composition may additionally comprise one or more anesthetic agents and one or more hemostatic agents.

In another aspect of the invention, a wound-healing or skin condition treatment dressing includes a gelling agent to thicken the mixture and to substantially prevent the composition from running and to release a desired amount of the dressing to the wound. Examples of useful gelling agents include, but are not limited to, natural polymers-proteins like gelatin, casein, collagen, egg whites, polysaccharides and semi synthetic polymers-cellulose subordinates such as carboxylmethyl cellulose, ethylcellulose, hydroxyethyl cellulose, hydroxypropyl cellulose, magnesium aluminum silicate, methylcellulose, sodium alginate, etc. The gelling agents are used in an effective, gelling amount of, for example, from about 0.01 to about 2.0% by weight, preferably from about 0.05 to about 1.0% by weight, based upon the desired effect.

Buckwheat honey/bacitracin formulations or compositions according to the present invention are useful for treating common chronic wounds, such as venous leg ulcers, diabetic foot ulcers, pressure ulcers, arterial ulcers, burns, non-healing surgical wounds, chronic rhinosinusitis and metritis. In addition, such formulations or compositions are also useful for treating abrasions, lacerations, minor cuts, scalds and burns, and other partial thickness wounds. The formulations or compositions are advantageously applied in a cream or ointment base for a period of time (e.g., several hours to several days) that are optionally impregnated into or associated with carrier dressing supports (e.g., fibrous gauze, hydrogel, foam, film, hydrocolloid, collagen, or alginate).

The buckwheat honey/bacitracin formulations or compositions can be applied directly to a wound as a cream or spray or administered on a bandage or dressing comprising a substrate. For example, a 5"×4" dressing containing the buckwheat honey/bacitracin formulation or composition could contain approximately four grams of pure strained buckwheat honey and from about 1 to about 20 to about 2000 units of bacitracin.

This "standard" formulation is useful applied to a substrate in variously sized bandages or dressings or in an ointment or cream from a tube or spray. This formulation will preferably be sterilized by gamma radiation. This sterilization process was chosen because gamma radiation (25 kGy) did not affect the properties of the buckwheat honey.

The present disclosure further provides a method for treating wounds or skin conditions. In some embodiments, the method includes contacting a wound or skin condition with any buckwheat honey/bacitracin formulation or composition disclosed herein wherein the composition includes a medicinal honey fortified with the natural non-peroxide antibacterial compound, bacitracin; a pharmaceutically acceptable carrier; 1-5% w/v and the natural non-peroxide antibacterial compound effective to reduce the number of viable microorganisms at a wound site. The buckwheat honey/bacitracin formulations or compositions are applied to a wound or skin condition, for example, in a liquid (e.g., by irrigating or lavaging the wound or skin condition with the liquid) or in a gel or an ointment. Liquid compositions provide immediate availability of the ions and bacitracin to the healing tissue. In contrast, gels or ointments provide regulated delivery of the ions, medicinal honey, and bacitracin to the healing tissue over a sustained period of time. In some embodiments, the buckwheat honey/bacitracin formulation or composition is applied to a wound dressing substrate, which is subsequently applied to the wound. Advantageously, a wound dressing including any of the compositions is contacted with the wound until it is healed (3-8 months) with wound dressing changes every 24-96 hours, thereby providing a moist environment enriched with fortified medicinal honey to facilitate healing of the skin. Similarly, a dressing comprising any of the formulations described herein can be contacted with a skin condition over a period of time with periodic changes.

In another aspect of the invention, a buckwheat honey/bacitracin formulation or composition can be provided in a tube or spray.

In another aspect of the invention, a wound-healing or skin condition treatment bandage or dressing comprises a substrate comprising a reinforcing fiber substrate material and a wound-healing or skin condition treatment formulation comprised of buckwheat honey and bacitracin.

In another aspect of the invention, a wound-healing or skin condition treatment substrate comprises an effective amount of the wound-healing or skin condition treatment formulation.

In another aspect of the invention, in a wound-healing or skin condition treatment substrate, the substrate material comprises acetate, cotton (medical gauze), or alginate.

In another aspect of the invention, a wound-healing or skin condition treatment substrate comprises a 5"×4" adhesive or non-adhesive bandage with from about 2 to about 8 grams of wound treatment dressing.

In another aspect of the invention, a wound-healing or skin condition treatment substrate comprises about four grams of buckwheat honey/bacitracin formulation or composition.

In another aspect of the invention, in a wound-healing or skin condition treatment substrate, the buckwheat honey/bacitracin formulation or composition is impregnated into a reinforcing fiber substrate for application to a wound or skin condition and is released therefrom.

In another aspect of the invention, a method of treating a wound on or in a patient comprises directly applying an effective amount of a wound treatment formulation comprised of buckwheat honey and bacitracin.

In another aspect of the invention, a method of treating a skin condition on a patient comprises directly applying an effective amount of a skin condition treatment formulation comprised of buckwheat honey and bacitracin.

In another aspect of the invention, a method of treating a wound or a skin condition on a patient comprises contacting the wound or skin condition with a wound-healing or skin condition treatment dressing comprising a reinforcing fiber substrate material and a wound-healing or skin condition treatment formulation or composition comprised of buckwheat honey and bacitracin. In one embodiment, the formulation is as follows:

(a) Buckwheat Honey 2-8 grams, preferably 4 grams
(b) Bacitracin 10-4000 units (preferably 20-2000 units)
(c) $H_2O$ (sterile), dependent on dilution The buckwheat honey/bacitracin formulation is preferably applied to an entire wound or skin condition. The treatment protocol includes complete evaluation of the wound or skin condition and clinical preparation of the wound or skin condition. For example:

Dressing Preparation:

An amount of 0.10 grams of bacitracin powder is dissolved in 1.0 cc sterile water, and the resulting solution is mixed with 4 grams buckwheat honey pure, strained. The mixture is impregnated into a 5"×4" acetate, non-woven medical grade substrate. Multiples of the buckwheat/bacitracin solution are made for multiple dressings. Each such substrate is protected with polyethylene liners applied to both sides, and each impregnated substrate is sealed individually in a foil pouch constructed of white polyester film fused to aluminum foil that constitutes the entire dressing package. The dressings are sterilized using a gamma radiation (minimum 25 kGy) and verified as sterile before use.

Clinical Procedure:

1. Clinical examination of patient's skin and condition of wound, including location, etiology, size, depth, viability of all tissues, odor, infection, culture, neurovascular status, and nutrition.

2. Debridement of all devitalize/necrotic, purulent tissue from the wound, using clinical judgment.

3. Wound irrigation.

4. Application of buckwheat honey/bacitracin dressing for complete coverage of wound, daily dressing, and appropriate and timely debridement/irrigation of wound (no soaking).

EXAMPLES

Objects and advantages of this invention are further illustrated by the following examples, but the particular materials and amounts thereof recited in these examples, as well as other conditions and details, should not be construed to unduly limit this invention.

Example 1

A composition comprises a buckwheat honey with high peroxide-induced and polyphenol-facilitated antimicrobial activity and an effective amount of bacitracin (100 units per gram of honey) to add non-peroxide antimicrobial activity, wherein each of the antimicrobial activities provides a different mechanism of antibacterial inhibition. This provides a broad spectrum antimicrobial activity effective to reduce the number of viable microorganisms at a wound site.

Example 2

In a composition similar to the composition described in Example 1, the honey is monofloral buckwheat honey that naturally generates 2-4 mM hydrogen peroxide and which naturally contains 275-575 gallic acid equivalents of polyphenol compounds per gram of honey, and wherein the amount of bacitracin is 100 units per gram of honey.

Example 3

A wound dressing comprises a composition of Example 1 or 2 and a support. The support is, for example, a hydrogel, a foam, a film, a hydrocolloid, an alginate, collagen, or a combination of any two or more thereof.

Example 4

Prior to treatment, a patient should be thoroughly informed of the nature of the treatment and any risks, and the patient should sign appropriate consent forms. In addition, a complete medical history and physical examination should be carried out prior to the initiation of treatment, medical or surgical Understanding the etiology of the wound and the factors that are affecting the wound healing process (i.e., weight bearing, vascular status, neuropathy, osteomyelitis, etc.) are important. Obviously, addressing such factors as these is extremely important in the successful treatment with all types of skin conditions and wounds. Multiple surgical procedures may be necessary to remove the devitalized, necrotic tissue and the surface exudate (biofilm) that may be present. Also, irrigation of the wounds can be performed at the same time the wounds are surgically debrided during hospitalization.

A combined buckwheat honey and bacitracin sterile dressing can be used as an outpatient dressing. This dressing should be changed daily, and each patient should be seen in the office at least once a week. At each visit the patient would be examined, wounds would be measured, photographs would be taken, and wounds would be debrided, as necessary, with sharp non-excisional technique.

The sterile buckwheat honey (4 grams) and bacitracin dressing (2.5% w/v) would be cut to the size and shape to completely cover a wound at each dressing change. The dressing would be applied directly to the surface of a wound entirely covering the wound. The dressing or bandage would be covered with at least one or more 4"×4" fibrous (cotton) gauze and wrapped with 4" fibrous (cotton) KLING® gauze dressings. Preferably the entire wound is covered at every dressing or bandage change in this manner whether in the office or at home. The patient's spouse or home health care provider should be educated on the proper technique for the dressing or bandage changes. The dressings or bandages should be kept clean and dry. No soaking or irrigation should be performed to the wound on an outpatient basis.

There could be indications where twice daily dressing or bandage changes are required. These indications could include increased wound drainage or increased wound desiccation.

Honey-MGO-Bacitracin Composition.

Wound-healing treatments using buckwheat honey and bacitracin have been described above. We now introduce a wound healing composition that improves upon the honey-bacitracin composition. A wound healing composition consisting essentially of buckwheat honey, a dilution of bacitracin in sterile water, and methylgloxal in an effective amount, promotes healing of a wound.

The present invention provides three additional exemplary wound healing compositions incorporating methylglyoxal (MGO). The first composition includes seasonally harvested raw, strained, monofloral buckwheat honey naturally rich in hydrogen peroxide (containing and/or capable of generating 2-4 mM concentration), polyphenols (275-575 gallic acid equivalents of polyphenol compounds per gram of honey) to which is added the natural antibacterial compound, methylglyoxal to a final concentration of 500-2000 mg per kg of final honey product. This MGO-fortified buckwheat honey has broad-spectrum antimicrobial activity effective to reduce the number of viable microorganisms at a wound site.

A second composition of the present invention incorporating MGO includes a pharmaceutically-acceptable carrier, an effective amount of an active mixture of inorganic minerals, and an amount of methylglyoxal (500-2000 mg per kg of final composition two product) that effectively reduces the number of viable microorganisms at a wound site. The active mixture of inorganic minerals include, but are not limited to, a magnesium salt, a potassium salt, a calcium salt, a zinc salt, and a rubidium salt, wherein each of the salts include a pharmaceutically-acceptable anion including bromide, chloride, citrate, and sulfate.

A third composition of the present invention incorporating MGO comprises a mixture of compositions 1 and 2 including a pharmaceutically-acceptable carrier, an effective amount of an active mixture of inorganic minerals, medicinal buckwheat honey that contains, or is capable of generating 2-4 mM hydrogen peroxide, and 275-575 gallic acid equivalents of polyphenol compounds per gram of honey, and methylglyoxal to a final concentration of 500-2000 mg per kg of composition 3 (buckwheat honey with MVE & MGO) such that the composition is endowed with broad spectrum antibacterial activity effective to reduce the number of viable microorganisms at a wound site. The active mixture of inorganic minerals includes, but is not limited to, a magnesium salt, a potassium salt, a calcium salt, a zinc salt, and a rubidium salt, wherein each of the salts includes a pharmaceutically-acceptable anion including bromide, chloride, citrate, and sulfate.

A wound dressing can be used with any of the above embodiments of the composition and a support. In any embodiment of the dressing, the support includes, but is not limited to, a fibrous gauze material, a hydrogel, a foam, a film, a hydrocolloid, an alginate, a collagen, or a combination of any two or more of the afore-mentioned.

In yet another embodiment, the present invention includes a method of treating a wound. The method includes contacting a wound with any of the above embodiments of the wound dressing.

FIG. 5 is a table listing the basic ingredients in the honey-MGO-bacitracin wound healing composition, with the suggested amounts, weights, and ranges, according to an embodiment.

A detailed description of the benefits of MGO, along with treatment examples, can be found in pending U.S. application Ser. No. 15/010,896.

While the present invention is described with respect to what is presently considered to be the preferred aspects, it is to be understood that the invention as claimed is not limited to the disclosed aspects.

Furthermore, it is understood that this invention is not limited to the particular methodology, materials and modifications described and as such may, of course, vary. It is also understood that the terminology used herein is for the purpose of describing particular aspects only, and is not intended to limit the scope of the present invention, which is limited only by the appended claims.

In light of the foregoing description, it should be recognized that embodiments in accordance with the present invention can be realized in numerous configurations contemplated to be within the scope and spirit of the claims. Additionally, the description above is intended by way of example only and is not intended to limit the present invention in any way, except as set forth in the claims. Modifications and changes to the invention should be readily apparent to those having ordinary skill in the art, which modifications are intended to be within the spirit and scope of the invention as claimed. It is also understood that the foregoing description is illustrative of the present invention and should not be considered as limiting. Components from one embodiment can be combined with another embodiment and remain within the spirit and scope of the invention. Therefore, other embodiments of the present invention are possible without departing from the spirit and scope of the present invention.

What is claimed is:

1. A wound-healing composition consisting essentially of:
    a buckwheat honey and methylglyoxal composition wherein the methylglyoxal is in an amount of from about 500 to about 2000 mg per kg of the buckwheat honey and methylglyoxal composition; and
    a dilution of one of: bacitracin and bacitracin zinc;
    in an amount effective to promote healing of a wound.

2. The wound-healing composition of claim 1, wherein the buckwheat honey is raw.

3. The wound-healing composition of claim 1, wherein the bacitracin is in a form of a white powder prior to dilution.

4. The wound-healing composition of claim 1 further comprising a gelling agent.

5. The wound-healing composition of claim 4, wherein the gelling agent is sufficient to thicken the mixture and to substantially prevent the wound-healing composition from running and to release a desired amount of the wound-healing composition to the wound.

6. The wound-healing composition of claim 1 wherein the bacitracin is in an amount from about 5 units to about 500 units of bacitracin per gram of buckwheat honey.

7. The wound-healing composition of claim 1, wherein the bacitracin is diluted in sterile water.

8. The wound-healing composition of claim 1, wherein the bacitracin is diluted in hydrochloride.

9. A wound-healing dressing comprising:
    a wound-healing composition consisting essentially of a buckwheat honey and methylglyoxal composition wherein the methylglyoxal is in an amount of from about 500 to about 2000 mg per kg of the buckwheat honey and methylglyoxal composition, a dilution of bacitracin, in an amount effective to promote healing of a wound; and
    a support.

10. The wound-healing dressing of claim 9 wherein the wound-healing dressing is capable of being replaced on a wound at least once.

11. The wound-healing dressing of claim 9, wherein the support is selected from the group consisting of a fibrous gauze material, a hydrogel, a foam, a film, a hydrocolloid, a collagen, an alginate, and a combination of two or more thereof.

12. The wound-healing dressing of claim 9 wherein the support is impregnated with a pharmaceutically-acceptable amount of the wound-healing composition.

13. The wound-healing dressing of claim 9 wherein the bacitracin is diluted in sterile water.

14. A method of treating a wound, comprising:
    providing a wound-healing composition consisting essentially of a buckwheat honey and methylglyoxal composition wherein the methylglyoxal is in an amount of from about 500 to about 2000 mg per kg of the buckwheat honey and methylglyoxal composition, a dilution of bacitracin in sterile water; and
    contacting the wound with a pharmaceutically-acceptable amount of the wound healing composition effective to promote healing of the wound.

15. The method of claim 14 wherein contacting the wound comprises applying the pharmaceutically-acceptable amount of the wound healing composition to skin.

16. The method of claim 15 further comprising a step of re-applying the pharmaceutically-acceptable amount of the wound healing composition to the wound daily until the wound is healed.

17. A method of treating a wound, comprising:
    providing a carrier dressing support impregnated with a pharmaceutically-acceptable amount of a wound healing composition consisting essentially of a buckwheat honey and methylglyoxal composition wherein the methylglyoxal is in an amount of from about 500 to about 2000 mg per kg of the buckwheat honey and methylglyoxal composition, and a dilution of bacitracin in sterile water; and
    applying the carrier dressing support to the wound, such that the wound healing composition is substantially in contact with the wound.

18. The method of claim 17, further comprising a step of applying a new carrier dressing support to the wound daily until the wound is healed.

19. The method of claim 17, further comprising a step of applying a new carrier dressing support to the wound every two days until the wound is healed.

20. The method of claim 17, further comprising a step of applying a new carrier dressing support to the wound every three days until the wound is healed.

* * * * *